United States Patent [19]

Berry et al.

[11] Patent Number: 4,661,458
[45] Date of Patent: Apr. 28, 1987

[54] CELL CULTURE SYSTEM

[75] Inventors: Eric S. Berry, Merrimack, N.H.; Bernard R. Danti, Lexington, Mass.

[73] Assignee: Cell Environmental Systems, Ltd., Merrimack, N.H.

[21] Appl. No.: 697,864

[22] PCT Filed: Aug. 22, 1984

[86] PCT No.: PCT/US84/01350

§ 371 Date: Oct. 2, 1984

§ 102(e) Date: Oct. 2, 1984

[87] PCT Pub. No.: WO85/01062

PCT Pub. Date: Mar. 14, 1985

Related U.S. Application Data

[63] Continuation of Ser. No. 527,997, Aug. 31, 1983, abandoned.

[51] Int. Cl.$^4$ .................. C12M 3/00; C12M 1/12; C12M 1/04; C12N 5/00
[52] U.S. Cl. .................. 435/284; 435/240; 435/285; 435/311; 435/313; 435/316; 210/321.2; 210/649; 210/651; 261/104
[58] Field of Search .............. 435/240, 241, 285, 286, 435/284, 311, 313, 316, 813; 210/321.2, 649, 651; 261/104

[56] References Cited

U.S. PATENT DOCUMENTS

| 3,323,653 | 6/1967 | Lacey | 210/321.2 |
|---|---|---|---|
| 3,695,444 | 10/1972 | Iaconelli | 210/321.2 |
| 3,734,851 | 5/1973 | Matsumura | 435/285 X |
| 3,827,565 | 8/1974 | Matsumura | 435/182 X |
| 4,069,157 | 1/1978 | Hoover | 210/651 X |
| 4,124,478 | 11/1978 | Tsien | 210/321.2 X |
| 4,225,671 | 9/1980 | Puchinger | 435/71 |
| 4,323,455 | 4/1982 | Tanaka | 210/321.2 |
| 4,416,993 | 11/1983 | McKeown | 435/243 |
| 4,540,492 | 9/1985 | Kessler | 210/651 |

FOREIGN PATENT DOCUMENTS

WO80/01043 5/1980 PCT Int'l Appl. ............. 210/321.3
1128181 9/1968 United Kingdom .

OTHER PUBLICATIONS

Feder, J. et al., *Scientific American*, vol. 248, No. 1, 1983, pp. 36-43.

Primary Examiner—Robert J. Warden
Assistant Examiner—Jeremy Jay
Attorney, Agent, or Firm—Iver P. Cooper

[57] ABSTRACT

A device is described which provides a totally enclosed and secure environment for the culture of cells and for the production of biologicals, pharmaceuticals, and other cell-derived products of commercial value. The device comprises several modules of differing functions: regulating the cellular growth environment, providing a suitable cell growth substrate or environment, or separating of desired product form interfering substances. Each module comprises a series of membranes separated by a solid support material which is channeled to provide a series of parallel capillaries for the flow of nutrients, environmental regulating fluids, or gas exchange. The structure and composition of the separating membranes limits the nature, rate, and size of the particular material exchanged across an individual membrane into or from an adjacent compartment. The capillaries are so dimensioned that the nutrients and gases are diffused over distances typical of human tissue.

4 Claims, 18 Drawing Figures

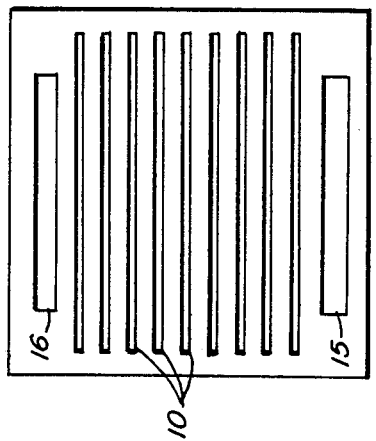
FIG. 14 SHEET 42
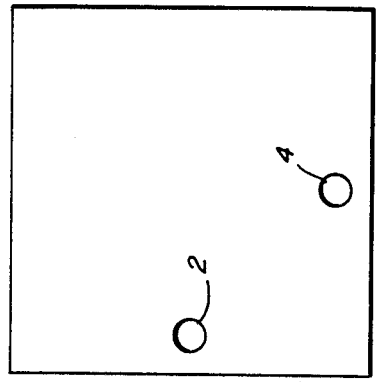
FIG. 17 SHEET 45
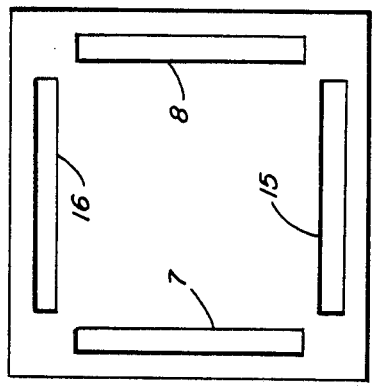
FIG. 13 SHEET 41
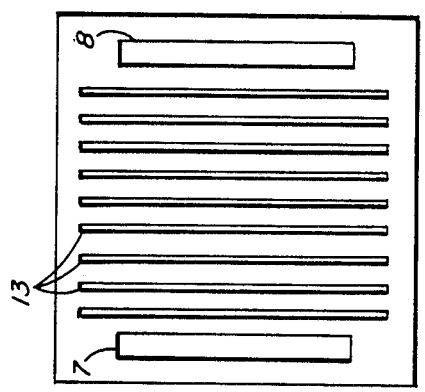
FIG. 16 SHEET 44
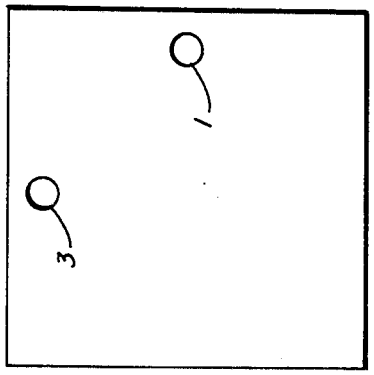
FIG. 12 SHEET 40
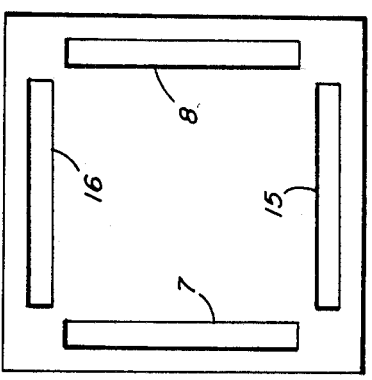
FIG. 15 SHEET 43

CELL CULTURE SYSTEM

RELATED APPLICATION

This application is a continuation of our application Ser. No. 527,997, filed Aug. 31, 1983, abandoned, entitled CELL CULTURE SYSTEM, the disclosure of which is incorporated by reference herein.

BACKGROUND OF THE INVENTION

This invention relates to a method and apparatus for the culture of cells. The cells to be cultured in this invention are prokaryotic and eukaryotic cells such as bacteria, yeast, plant, animal and human cells. These cells may be derived in any manner, that is, isolated from nature, mutated, in the naturally-occurring form, genetically engineered or modified, transformed or non-transformed, hybrids formed by fusion between portions of cells or whole cells of the same or different species. These cells may be attached to the substrate, grown in suspension, or in suspension attached to another substrate, such as microcarrier bead. The cultures may consist of a single cell line or a plurality of cell lines of the same or different species.

Conventionally, cells have been attached to and grown on the interior surface of glass or plastic roller bottles or tubes or on culture plates. This approach does not permit high-density growth of cells and requires large amounts of nutrient medium, in most cases. Use of these systems is also labor intensive.

U.S. Pat. Nos. 4,189,534 and 4,266,032 describe the growth of cells on tiny beads referred to in the art as microcarrier. Microcarrier systems have several disadvantages, such as cell damage from collision of beads, mingling of the desired cell product with the nutrient medium, cell fragments and other contaminants, and the difficulty of achieving continuous production of the desired product.

It is also known that cells may be grown on or near hollow or solid fibers. See U.S. Pat. Nos. 3,883,393; 3,997,396; and 4,087,327; 4,220,725; 4,391,912 also J. Feder and W. R. Tolbert, "The Large-Scale Cultivation of Mammalian Cells", Scientific American, Vol. 248, No. 1 and Amicon Technical Data Publication Number 442C, "Vitafiber TM Artificial Capillary Systems for Tissue Culture". Typically the nutrient medium is passed through the hollow fibers and diffuses through the lumen thereof into the cell growth space and extracapillary space bounded by an envelope. These capillaries are susceptible to mechanical vibration and shock. The location of the cells is not closely constrained and the cells most distal from the fibers may not be well nourished. Large volumes of nutrient are typically utilized.

U.S. Pat. No. 4,225,671 describes a cell culture apparatus in which a stack of parallel flat membranes defines separate, typically alternating, cell culture medium, and cell growth spaces. These membranes are spaced widely apart (2 mm), so excessive quantities of nutrient must be provided to ensure the nourishment of the cells most distal from the membrane. Since the membranes are supported only at their edges, the maximum surface area of each membrane is limited by the tensile strength of the membrane. Thus, production capacity is limited. In addition the membrane is not designed to restrict the flow of the cell product into the nutrient medium and the product is collected in that medium. Because the cell product is mingled with the culture medium, product, recovery and purification is complex and results in a low yield of product.

U.S. Pat. No. 3,948,732 shows a spacer structure which is convoluted to offer internal support to the substrate surfaces. It does not, however, recognize the importance of a fluid path separate from that of the nutrient medium.

One object of the invention is to provide a closed sterile system for cell culture in order to prevent both exposure of personnel to the cells and the contamination or infection of the cell culture by wild strains entering from the outside environment.

Another object of the invention is to provide a system for cell culture which more closely approximates a continuous system than those known previously, thus increasing the average or steady-state output of product and minimizing opportunities for contamination.

Another object of the invention is to simulate the supply of nutrient to and exchange of gases by cells in vivo, wherein cells are typically less than 200 microns from the capillaries, the sources of nutrients and respiratory gases.

Another object of the invention is to provide a cell culture assembly in which the maximum distance between a cell and the nearest source of nutrients and dissolved gases approximates that typical of the cells in vivo.

Another object of the invention is to provide a cell culture assembly which can be economically manufactured.

Another object of the invention is to provide a cell culture assembly and cell culture system which lends itself to the growth of cells at high densities.

Another object of the invention is to provide a cell culture assembly and cell culture system in which fluctuations in cell growth and production of the desired product are reduced.

Another object of the invention is to provide a cell culture system in which nutrient supply, heat transfer, gas transfer, cell growth and product collection functions are integrated.

Another object of the invention is to provide a cell culture system in which those functions are performed by separate modules of similar construction, and thus more economical to fabricate.

Another object of the invention is to provide multi-layered modules for cell culture and related purposes which can be assembled by lamination into an essentially rigid block structure.

Another object of the invention is to provide a cell culture assembly and cell culture system in which the nutrient medium circulation path is independent from the path carrying the cell product, metabolic products from the component of the culture medium and the cells themselves.

Another object of the invention is to provide a cell culture system in which the cells' environmental conditions are continuously monitored and any departures from the desired range of value in any environmental parameter are automatically indicated and corrected.

Another object of this invention is to provide a laminated structure for the fluid paths such that high strength and reliability are attained.

Another object of this invention is to provide a laminated structure that may be increased in size to accommodate large scale cell culture.

Another object of this invention is to provide a cell culture assembly which does not require large volumes of medium.

The aforesaid objects as well as other objects of the present invention will be made more apparent by the following description, claims and drawings.

SUMMARY OF INVENTION

In accordance with these objects, the cell culture system comprises a series of connected modules which provide a favorable location for cell growth and maintain the environment of the cells so as to promote continued production of the desired product. Typically, the modules will be heat transfer, gas transfer, cell culture and cell-product separation modules. Multiple separate and independent circulation loops exist within the cell culture system. In a given module only two of these circulation loops are operational. Means are provided for continuous circulation of nutrient culture medium through all of these modules (except for the cell-product separation module). In the second circulation path separate and independent means (secondary or auxiliary loops) exist for (a) the passage of gases through the gas transfer module, (b) the passage of heat through the heat transfer module, (c) the introduction of cells into the cell culture module, and (d) the withdrawal of product from the cell growth module into the cell-product separation module. In addition, a separate and independent means exists for the transfer of the separated cell product(s) into a collection vessel to be held for further processing.

The modules are preferably fabricated in a similar manner to achieve similar structures. The common structure of the preferred modules is described below as the basic module. The various modules differ from the basic module in the nature of the separator sheets 11 of FIG. 4 or sheets 43 of FIG. 15, and in the nature of the fluids circulated in the auxiliary circulation system. All of the modules except the cell-product separation module are connected and serviced by the nutrient medium circulatory system.

The modules of the present invention provide a large surface area, relative to the volume occupied by the modules, for cell growth and or attachment. The modules of the present invention are sterile, disposable, and replaceable. In accordance with one of the features of the system there is provided a sterile, disposable temperature control module. This feature allows a constant temperature fluid to circulate on one side of the non-porous membrane to control the temperature of the growth medium on the opposite side of the membrane without contact or contamination. In accordance with another feature of this invention, there is provided another sterile, disposable module for the exchange of gases with the growth medium by diffusion of the gases across either a hydrophobic or hydrophilic membrane. In accordance with another feature of this system, there is provided another sterile, disposable module to provide an environment and source of suitable growth medium. The cells are then cultivated on the opposite side of the membrane free from many of the contaminates in the growth medium. In accordance with another feature of this invention, there is provided another sterile, disposable module that incorporates a microporous filter to retain any free cells in the case of substrate attached cells or in the case of suspension cells to retain the free mobile cell culture and provide a closed loop thus allowing circulation back through the growth module. The soluble products are then eluted off the opposite side. In accordance with another feature of the system the available contact surface area of the modules may be varied from 200 sq cm to 80,000 sq cm. In accordance with another object of this system there is provided a means for growing cells in a totally enclosed environment to decrease the probability of contamination of the external environment by cells or cell products, and to decrease the probability of contamination of the cellular environment by foreign particulate matter or biological organisms. This system which is comprised of individual disposable modules also provides a means for disposing of individual contaminated units in an efficient manner which minimizes the threat to the environment. Further, since the system allows the culture of high densities of cells in a small volume of necessity for handling large numbers of culture vessels and the medium required to feed them is reduced resulting in a lowered risk of compromising the laboratory and surrounding environment. In accordance with another object of this invention there is provided a selective semi-permeable membrane to separate the cell nutrient flow path from the cell growth and cellular production path and thus permits the collection of cell product in a more highly concentrated form free of certain nutrient medium components which would dilute the cell product were the two pathways common. In accordance with another object of this invention there is provided a means for the collection of the concentrated cell product that permits less complicated and less costly methods to be used in the recovery and purification of the product because smaller volumes must be processed. In addition the use of a highly concentrated starting material for recovery and purification generally promotes more efficient recovery of final product in terms of purity and recovery.

In accordance with another object of this invention there is provided a means for periodic reversal of the nutrient medium flow and cell production collection flow to provide more efficient exchange of nutrient medium and cell waste products and thereby permit growth of greater cell numbers and thus increase the amount of product produced per unit of cell growth area.

In accordance with another object of this invention there are provided assemblies wherein the boundaries of the channels constrain the cells and fluids in such a manner that the cells are never more than 200 microns from the nearest source of nutrients.

Other features and benefits of the invention will be seen as the description of each module progresses, in conjunction with the following drawings.

FIG. 1—Cover plates top view
FIG. 2—Auxiliary primary sheet top view
FIG. 3—Auxiliary secondary sheet top view
FIG. 4—Separator sheet top view
FIG. 5—Media secondary sheet top view
FIG. 6—Media primary sheet top view
FIG. 7—Pictorial view basic module construction
FIG. 8—Schematic view of total system
FIG. 9—Cross-Section Part of FIG. 7
FIG. 10—Schematic of microprocessor
FIG. 11—Pictorial view basic module with perpendicular circulation
FIG. 12—Top cover plate top view
FIG. 13—Media and Auxiliary spacer sheet
FIG. 14—Auxiliary capillary sheet
FIG. 15—Separator sheet FIG. 16—Media capillary sheet
FIG. 17—Bottom cover sheet top view
FIG. 18—Exploded view basic module with perpendicular circulation

DETAILED DESCRIPTION OF INVENTION

Basic Module

The basic module preferably has a large number of narrow parallel channels which are preferably formed by the superposition of the various sheets (FIGS. 1–6) of the assembly, as more fully set forth below.

Figure 3:
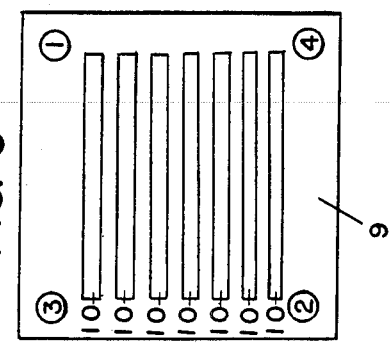
Figure 6:
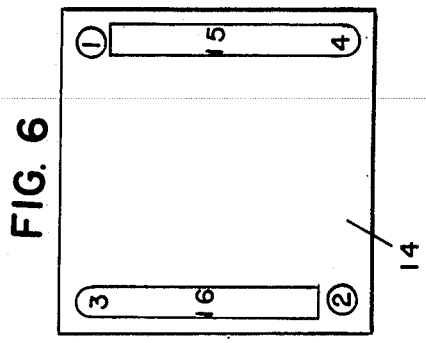
Figure 2:
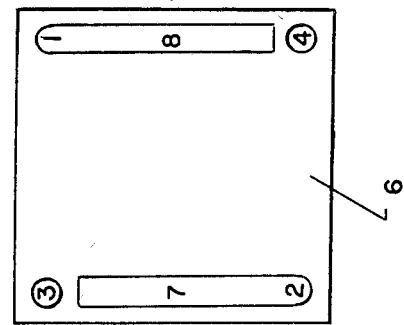
Figure 5:
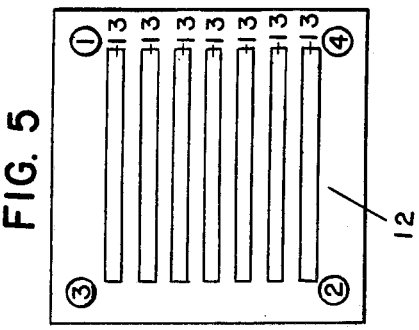
Figure 9:
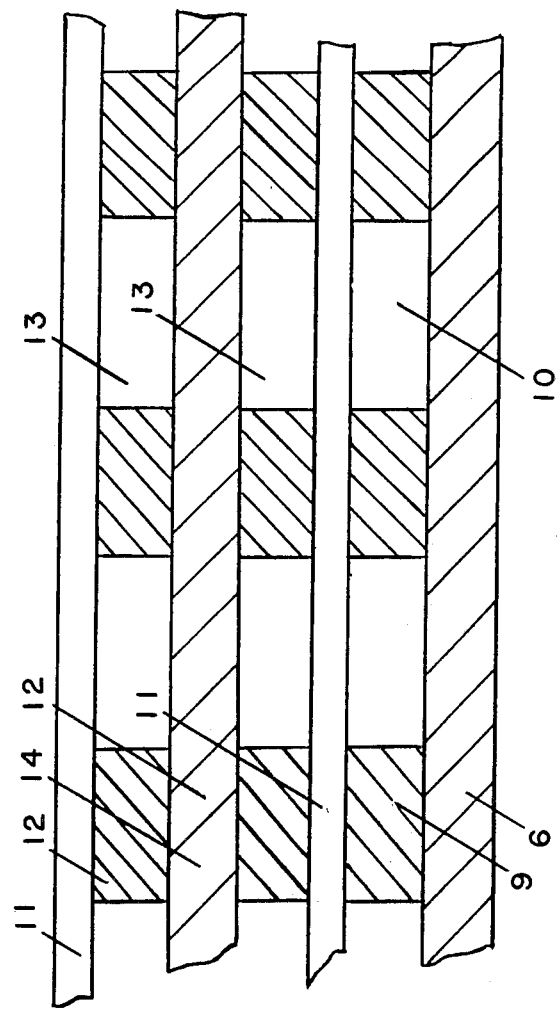

In one embodiment of the invention, a secondary sheet 9, as shown in FIG. 3, has a plurality of narrow, parallel slots 10. This sheet is disposed between a separator sheet 11 (FIG. 4) and a primary sheet 6 (FIG. 2). As can be seen in FIG. 9, these three sheets cooperate to bound a plurality of channels 10 in sheet 9 whose depth is that of sheet 9. These channels 10 will be referred to by reason of their function, as auxiliary capillaries. The number, spacing, width and depth of these auxiliary capillaries is preferably chosen in view of the function of the module in which they appear. The result is that numerous parallel channels are formed on each side of the separator sheets. The flow through the capillaries is sealed from and independent from the flow on opposite side of each separator sheet 11; although, the nature of the separator sheet 11 may allow exchange of appropriate and desired substances between the chambers. Similarly, a secondary sheet 12 (FIG. 5) is disposed between a separator sheet 11 and a primary sheet 14 (FIG. 6) to create channels 13, the media capillaries. As can be seen in FIG. 9 these three sheets cooperate to bound a plurality of channels 13 in sheet 12, whose depth is that of sheet 12; and that said channels are separate and independent and communicate across said membrane.

The disposition of the auxiliary primary sheet 6 (FIG. 2) between the secondary sheet 9 and either a cover plate 5 or another secondary sheet 11 creates two larger channels 7 and 8, referred to as the auxiliary vein 7 and the auxiliary artery 8.

Similarly, the disposition of the media primary sheet 14 between the secondary sheet 12 and either a cover plate or another secondary sheet 11 creates a media vein 15 and a media artery 16.

Figure 1:
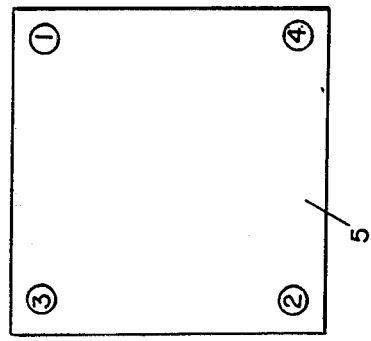
Figure 7:
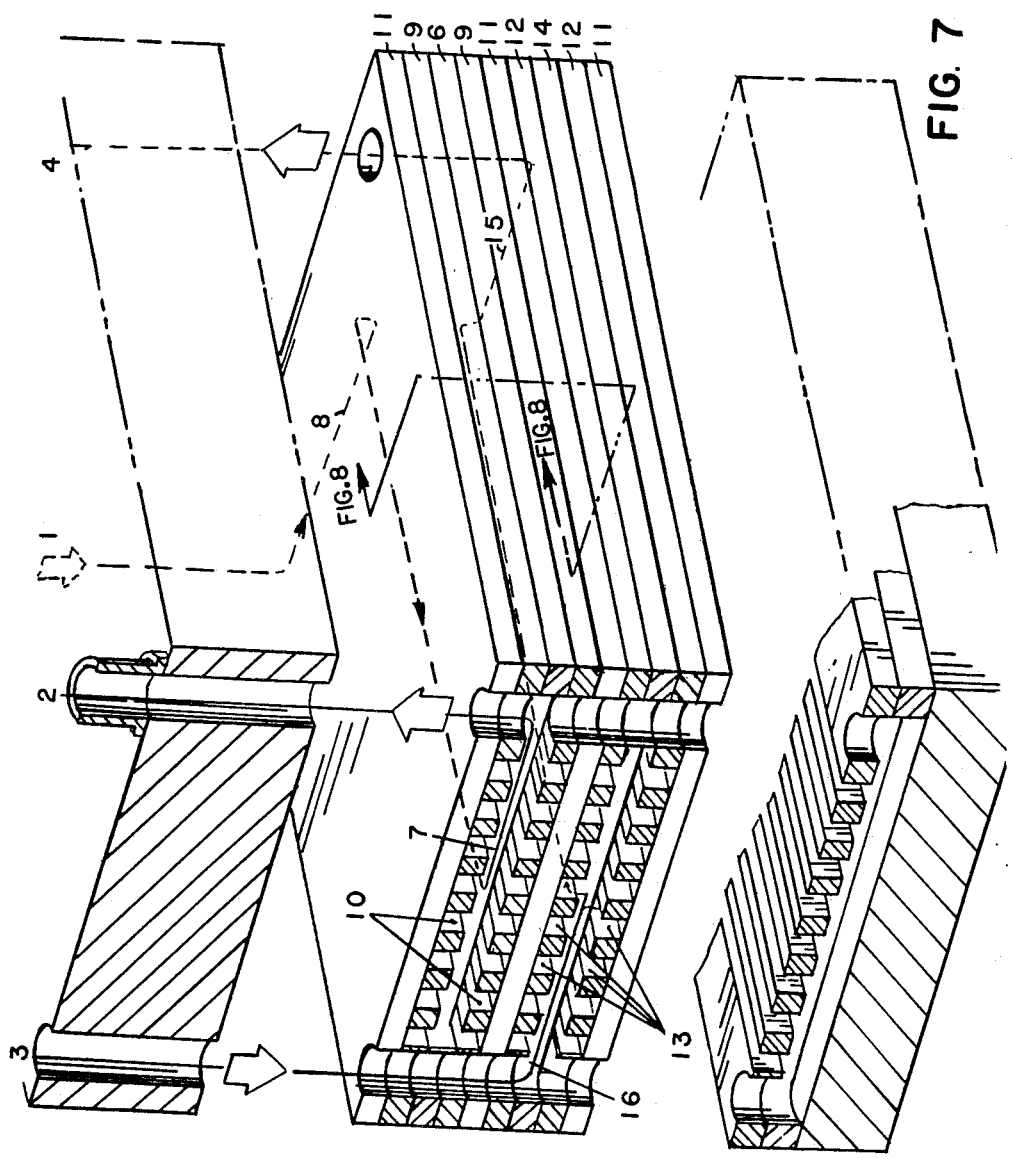
Figure 8:
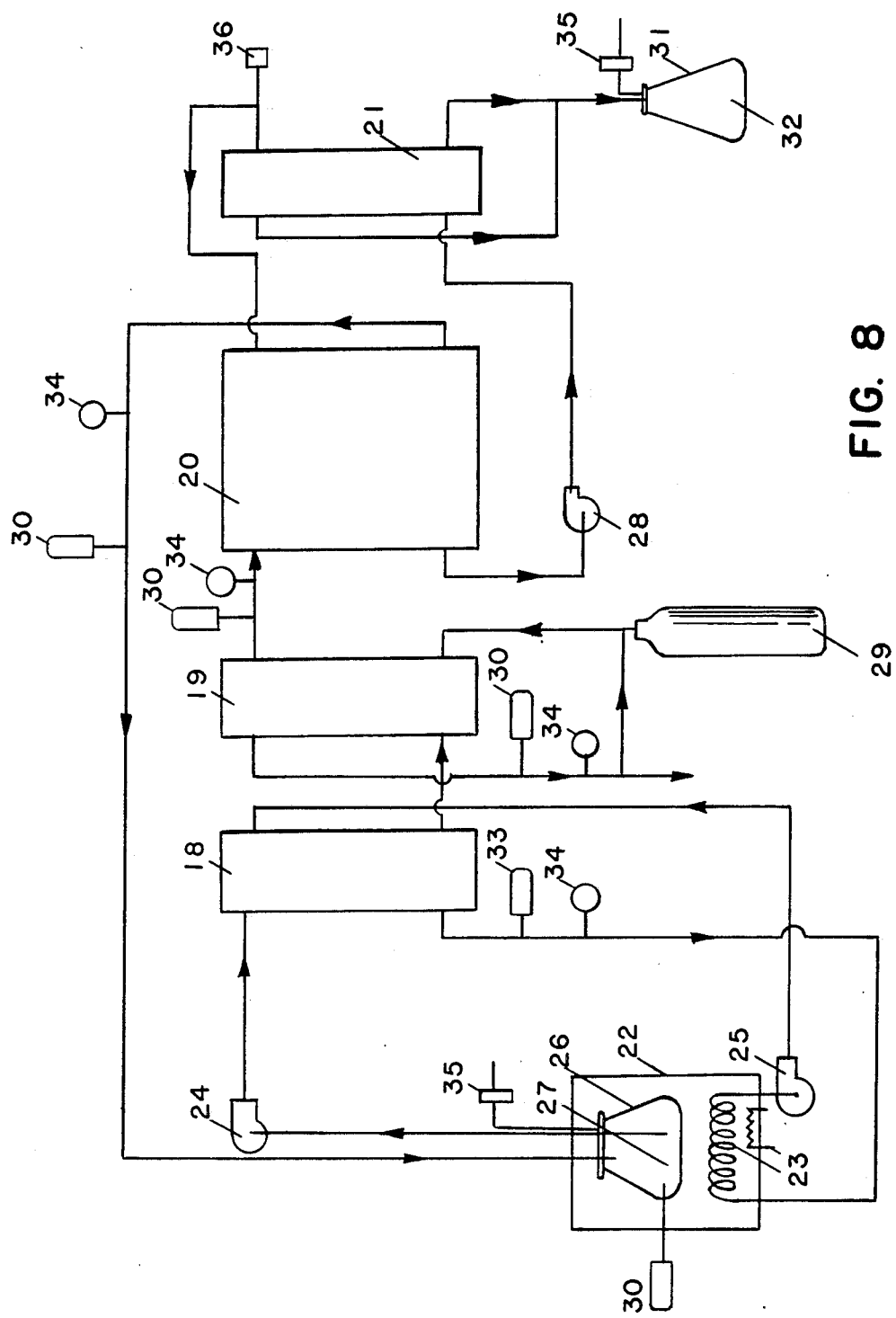

Cover plate 5, as shown in FIGS. 1 and 7, has as auxiliary inlet 1, an auxiliary outlet 2, a medium inlet 3, and a medium outlet 4. In FIG. 7, only the ports on the top cover plate are in use, while the ports on the bottom cover plate are capped. It is possible to use some top plate ports and some bottom plate ports as shown in FIG. 8, moreover the precise location of these outlets and inlets may be varied as deemed appropriate. Note that the terms "top" and "bottom" are for convenience and do not refer to the orientation of the module. The modules are preferably constructed by lamination of the sheets. It is not necessary that all of the sheets comprising the module be made from the same material.

Although in the configuration shown FIGS. (7–9) the media and auxiliary capillaries are substantially parallel to each other it can be seen in FIGS. (11, 18) that in a second embodiment these channels may run substantially perpendicularly. In the second embodiment only one separator sheet 41 FIG. (13) may be required due to the perpendicular construction. It can be seen in FIG. 13 that spacer sheet 41 contains the arteries 16, 8 and veins 15,7 requiring two sheets, sheets (6,14 FIGS. 2, 6) in the first embodiment.

It is preferable, but not necessary, that the media and auxiliary capillary channels have the same dimensions. The channels in the appropriate sheets may be aligned with each other, or they may be offset in the direction perpendicular to their longest dimension. This offset may increase mechanical strength. The perpendicular construction has a similar advantage.

Figure 18:
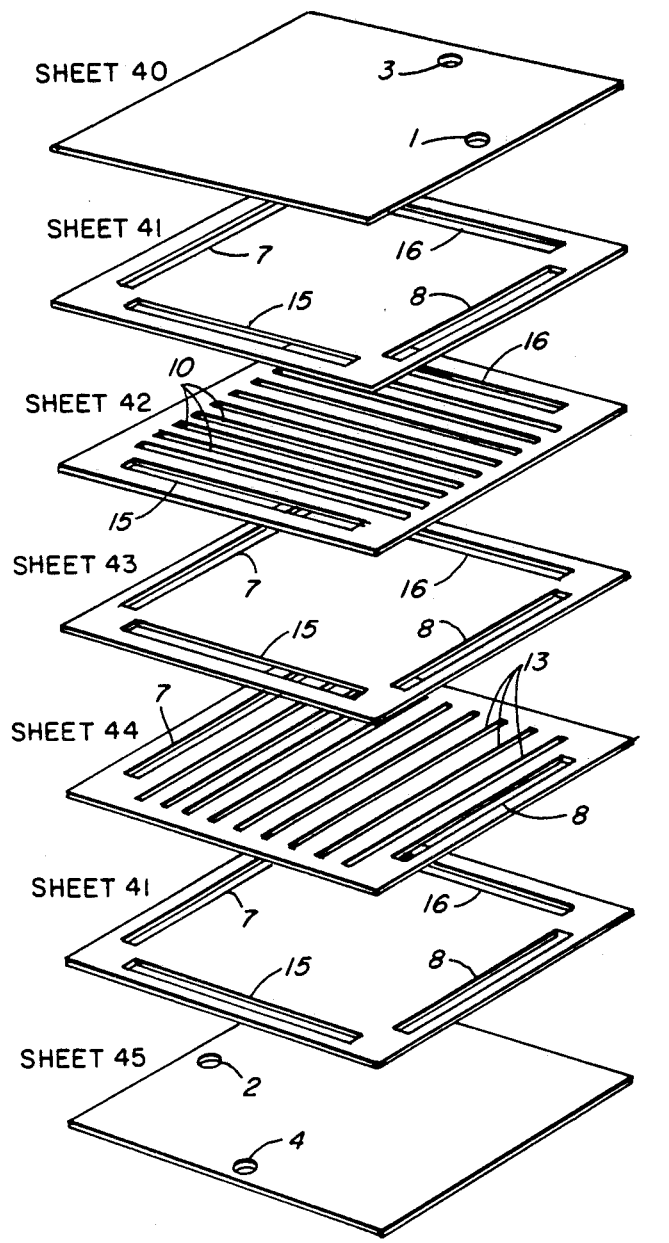

Although in the configuration shown in FIG. 18 there is only one set of media and auxiliary capillaries; it can be seen in FIG. 18 that a large number of narrow parallel channels are formed by the superposition of various sheets 41–44 FIGS. (13–16) as set forth below and previously described in the basic module. The superposition of an additional separator sheet 43 and media capillary sheet 44 between the spacer sheet 41 FIG. (18) and the auxiliary capillary sheet 42 FIG. (18) provides additional media capillaries and a complete set of veins and arteries.

Similarly the superposition of an additional separator sheet 43 and auxiliary capillary sheet 42 between the media capillary sheet 44 and the spacer sheet 41 FIG. (18) provides additional auxiliary capillaries and another complete set of veins and arteries.

As in the basic module description the flow through the capillaries is independent from and sealed from the flow on the opposite side of separator sheet 43; although, the nature of separator sheet 43 may allow the exchange of appropriate and desired substances between the chambers as shown in FIG. (8).

In the media circulatory system, media enters fluid inlet 3 sheet 40 FIG. (12) and flows into the media artery 16 of FIGS. (13, 14, 15). It then is distributed through media capillaries 13 sheet 44 FIG. (16). If the separator sheet 43 FIG. (15) is a permeable membrane, then certain substances will permeate separator sheet 43 which separates media capillaries 13 of FIG. 16 and the auxiliary capillaries 10 sheet 42 of FIG. 14. Media leaves the media capillaries 13 through media vein 15 of FIGS. (13, 14, 15) and then leaves through media outlet 4 sheet 45 FIG. (17). Fluids permeating separator sheet 43 FIG. (15) are collected first in the auxiliary capillaries 10 FIG. (14) and are thence extracted from auxiliary inlet and auxiliary outlet 1,2 FIGS. (12, 17) through the arteries and veins 8,7 FIGS. (13, 15, 16).

Suitable culture media for the cultivation of various types of cells are known and may be used in the method and apparatus of this invention. Culture media typically are composed of assimilable sources of elements such as carbon, nitrogen, and phosphorus, and may include amino acids and blood serum, by way of example. The composition of the culture medium may be varied from time to time to control cell metabolism and reproduction. In addition, the pH of the medium may be controlled or monitored.

The function of the auxiliary circulatory system varies from one type of module to another. Fluid enters at auxiliary inlet 1 and flows into the auxiliary arteries 8 of FIG. 3. It is then distributed by auxiliary capillaries 10 of FIG. 3. The fluid is collected by the auxiliary veins 7 and withdrawn through auxiliary outlet 2.

The number of veins, arteries and capillaries in the module is proportional to the number of separator sheets 11 FIG. (4) or sheets 43 FIG. (15) in the module. Typically, a single module will contain 2 to 400 separator sheets.

Preferably each secondary sheet defines a minimum of 20 capillaries 10 or 13 (FIGS. 3, 14 and 5, 16 respectively), and these capillaries are, 7 thousandths of an inch (178 Microns) deep and no more than 25 centimeters in length. The width and spacing are less important, but we have sucessfully used a width of 760 to 1650 microns, and a spacing of 1270 to 2540 microns. The width, depth and spacing may be varied, in response to the growth needs of the cells. The minimum dimensions are defined by the typical dimensions of a single cell of the type of cells to be cultivated. The maximum dimension can not be so great as to unduly limit the nourishment of cells at the distal wall of the cell growth spaces from the membrane. In addition, as the width is increased, the strength of the structure is weakened. The depth should be substantially similar to the maximum distance separating cells from capillaries in vivo, and it is thought that 500 microns is the upper limit if the advantages of this structure are to be achieved. Preferably, it should be less than 200 microns, however the depth may be increased to 1000 microns to accomodate "micro-carriers", or other large hybrid cells.

The cell culture spaces should be so dimensioned and oriented that the distance between a cell in a distal region of said spaces from the vascular network defined by the culture medium spaces and connecting passages is less than or substantially similar to that typical of the tissues or organs in which a cell of the type grown is found in vivo.

The terms vein, arteries and capillaries are utilized hereto suggest the relative dimensions of these channels and the veins, whether they carry fluid into or out of the module, and to emphasize that the system and its component modules are meant to simulate certain of the characteristics of the supply of nutrients to and exchange of gases by cells in vivo.

The term fluid is here used to refer to both liquids and gases, whether pure or mixed, and to include liquids or gases carrying substances in solution or in suspension.

The following will be a description of the heat transfer module, gas transfer module, cell growth module and the cell-product separation module. It should be assumed that all modules will have the structure of the basic module, except as set forth below.

Heat Exchange Module

In the heat exchange module 18, the separator sheet 11 FIG. (4) or separator sheet 43 FIG. (15) is nonporous, and preferably of polysulfone, or other suitable film with good heat transfer characteristics (greater than 2.8 cal/sec per square centimeter). The auxiliary arteries, veins and capillaries conduct a heat transfer fluid, which mediates the temperature of the nutrient medium 27 in the nutrient medium capillaries 13 of module 18 as a result of heat transfer across separator sheet 11 or sheet 43.

The temperature at which the culture medium is maintained may be varied in accordance with the growth characteristics of the cells, and hence the heat transfer fluid may have either a heating effect of a cooling function. The fluid temperature is maintained in a conventional manner.

Gas Exchange Module

In the gas exchange module 19 the separator sheet 11 FIG. (4) or separator sheet 43 FIG. (15), is a porous film which may be either hydrophobic or hydrophilic in nature; and which has the ability to flow at least $7*10E-6$ ml/min-sq-cm-mm Hg. The auxiliary arteries conduct life-sustaining gas into the auxiliary capillaries 10. These gases then pass across the separator sheet 11 or 43 into media capillaries 13 to be carried eventually to the cells in module 20. Waste gases carried by the medium 27 from module 20 are carried eventually to module 19 where they pass across sheet 11 or 43, into the auxiliary capillaries 10 and thence are removed from the system via auxiliary veins of the gas module 19.

The gas mixture circulated by the gas transport module may be air, or an artificial mixture of various elemental and compound gases.

The term "cell culture" encompasses both conditions for cell conservation and metabolic production and conditions providing for cell growth.

Cell Growth Module

Figure 4:
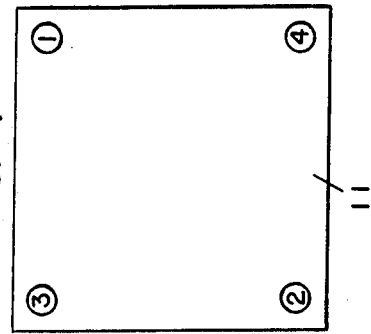

In the cell culture module 20, the separator sheet 11 FIG. 4 or separator sheet 43 FIG. 15 is a porous film which is hydrophilic in nature; but which has a known and selected porosity. The porosity is such as to restrict the flow of substances of known molecular weights and/or charge, whose passage across the separator sheet 11 or sheet 43 from the media capillaries into the auxiliary capillaries is not desired. For example, a membrane having a 10,000 dalton nominal cutoff may be used to restrict the entrance of serum components including proteins having nominal molecular weights more than 10,000 daltons into the cell growth spaces, defined by the auxiliary capillaries. Likewise products which have a molecular weight greater than 10,000 daltons produced by the cells and secreted into the extra-cellular medium are restricted from entering the nutrient medium flow path. Membranes having higher or lower molecular weight cutoffs (range $1000 \rightarrow 1 \times 10E7$) can be used to restrict the transfer of desired molecular weight materials from adjacent chambers. Similarly different charge densities may be applied to the membranes to restrict the transfer of charged materials across adjacent membranes. Thus standard culture media containing unnecessary components may be utilized without mingling these components with the desired product.

By providing a separator sheet having a desired molecular permselectivity, passage of chemical species across the sheet is controlled.

The auxiliary artery conducts new cells suspended in extra-cellular fluid, into the auxiliary capillaries of module 20, the cell growth or culture spaces, where they may adhere to the walls of the capillaries or may remain in suspension or attached to microcarriers.

These cells are nourished by nutrients passing across sheet 11 or sheet 43 from the the nutrient media capillaries. Product is removed through the auxiliary veins and does not mix with nutrient media 27. Once the cells are aseptically introduced into the cell culture assembly, other undesired cells cannot enter the cell culture spaces across the membrane from the nutrient medium spaces. Consequently, contamination of the cell culture spaces is prevented. (Of course, since the nutrient medium is continuously circulated within a closed system, it is unlikely that the medium would be contaminated in the first place.)

Cell-Product Separation Module

In the cell-separation module 21 the separator sheet 11 FIG. (4) or separator sheet 43 FIG. (15) is a porous membrane which is hydrophilic in nature, and has the ability to retain particles of a known size. For example, a membrane having a pore size of 5 microns could be used to restrict cells having a mean size of greater than 5 microns to the cell growth module. This pore size would permit transfer of the cell products across the membrane into a collection means, which may be a holding vessel or additional processing apparatus. The conduit 16 of module 21 distributes fluid received from inlet 3 (sometimes referred to as media inlet 3) to the capillary channels 13 (sometimes referred to as media capillaries). The fluid 32 then moves along separator sheet 11 or 43, which retains particles greater than the rated size. Part of this fluid 32 passes through the membrane and is collected in the auxiliary channels 10 and collected in the auxiliary conduits 7 and 8 thence passed to collection means 31 from auxiliary connections 1 and 2.

The Cell Culture System

Referring to FIG. 8 there is shown an incubator 22 containing heat transfer fluid 23, maintained at a suitable temperature. The heat transfer fluid in conduit 23 is pumped to inlet 1 of the temperature control module 18 by pump 25 and returned to the incubator through sensor blocks 33, 34 from outlet 2. Controlled gases from reservoir 29 are introduced to auxiliary inlet 1 of module 19 by pressure and exit through sensor 30, 34 from outlet 2 module 19. Located in the incubator 22 is a media reservoir 26 containing medium 27. Medium 27 is pumped using a diaphraghm pump 24 to inlet 3 of the temperature control module 18 then from outlet 4 of module 18 to inlet 3 of the gas exchange module 19. Collected at outlet 4 of module 19; and fed to inlet 3 thought 30, 34 of the cell growth module 20, and finally it is collected at outlet 4 of module 20 and returned to reservoir 26, through sensor block 30, 34. The cells are introduced to inlet 1 of the cell growth module 20. The extracellular fluid which includes both product and loose cells, is pumped to inlet 3 of the cell/product separation module 21, by pump 28 from outlet 2 module 20. The loose cells and product are separated by separator (11 or 43) and the product is conducted from inlet 1 and outlet 2 of module 21 to collection means 31. The remaining extracellular fluid is returned to inlet 1 module 20 from outlet 4, module 21. Alternatively the cells themselves may be removed through a valve 36 after outlet 4 of module 21. This allows the harvest of cells to be ruptured to release product(s) not normally secreted by the cells.

Despite the use of the term "continuous process", it should be understood that, on occasion the culture medium and other fluids may be replaced.

Figure 10:
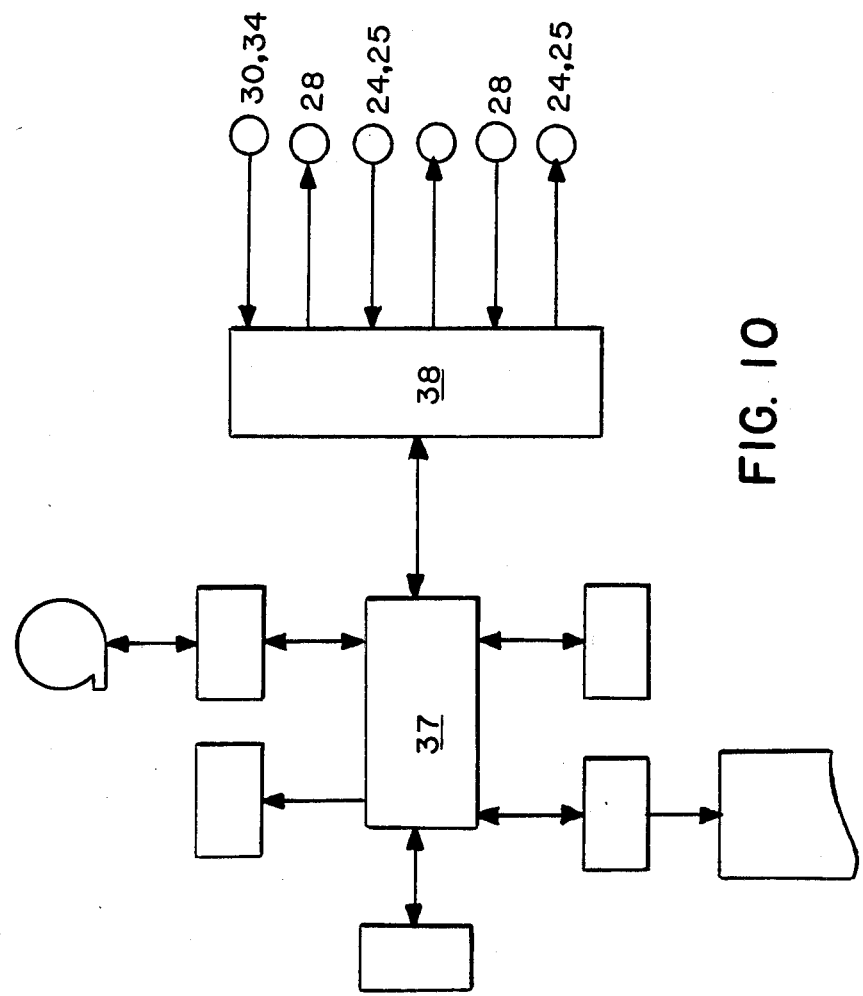
Figure 11:
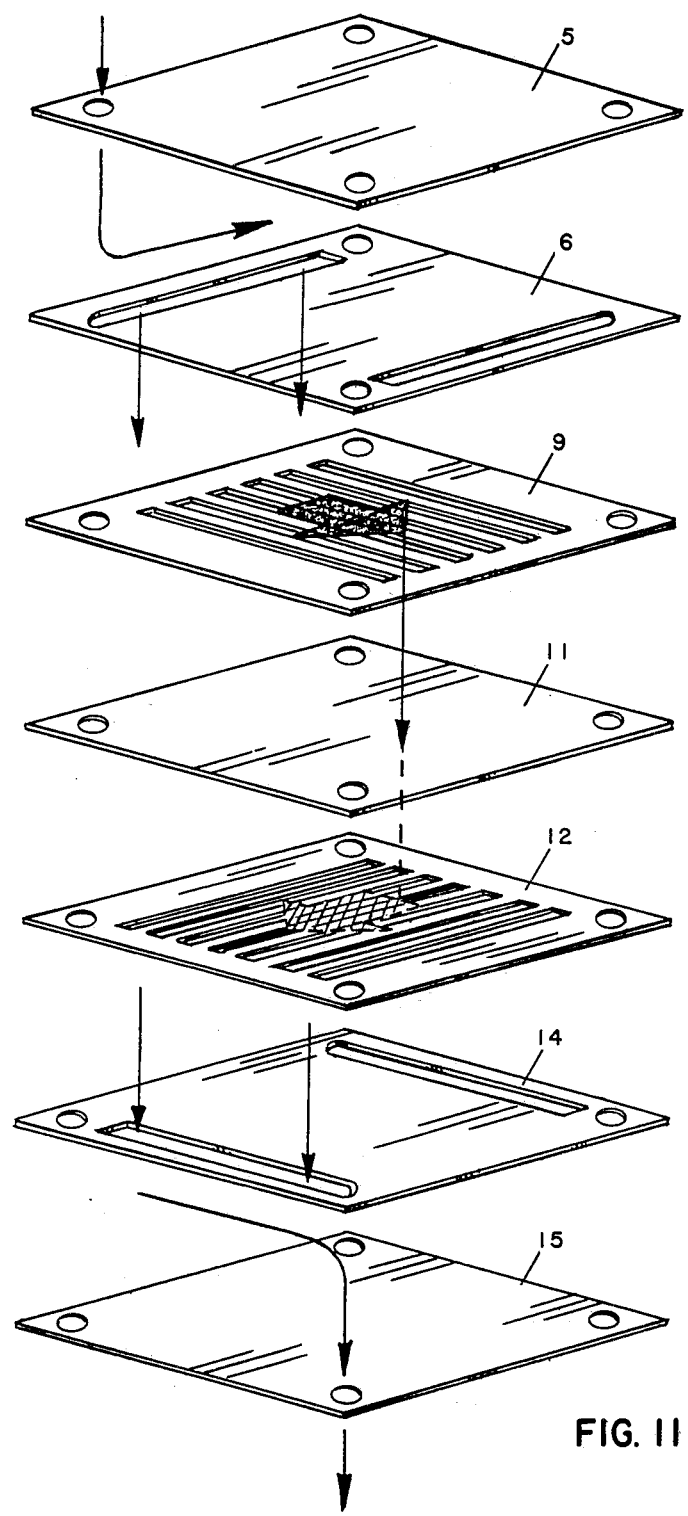

Preferably, an automatic control subsystem is provided. A microprocessor 37 of FIG. 10 is connected to sensor blocks 30 and 34 via an A/D, D/A converter 38 so as to monitor the pressures, gases, Ph, temperature, and dissolved gas content and to pumps 24, 25 and 28 such that it will monitor, alarm, and react if any of the state variables enter an unacceptable range. This is especially important for preserving the safe atmosphere for the personnel using the equipment. Alarm means are connected to the microprocessor and triggered when an unacceptable state is reached. By control means connected to said pumps, it causes corrective measures to be taken. This automated system enhances the safety of the closed system by virtue of the controls, alarms and ability to shut down the system on detection of failure. This feature thus provides an additional safety factor for the personnel in the production environment.

While in FIG. 7 only a single module of each type is shown in the cell culture system, it should be understood that additional modules of any type may be added to the system. In addition, it should be understood that the system may be simplified (though at a cost to its ability to function automatically for long periods of time) by omitting certain of the modules.

While a cell culture system preferably employs modules of the modular construction described herein, any of the individual modules may be used in a cell culture system which is not characterized by modularity.

While the particular system description of this invention has been shown and described, various modifications will be apparent to the user's skill in this area and the art of tissue culture and it is therefore not intended that this invention be limited to the disclosure herein contained, and that departures may be made therefrom within the scope and spirit of this invention.

We claim:

1. A cell growth system for the growth of cells and the recovery of desired metabolic products which comprises
   (a) a culture medium circulation means providing a plurality of separate, parallel medium channels into which the culture medium is distributed and from which it is withdrawn;
   (b) a cell growth means providing a plurality of separate, parallel culture channels into which cells may be introduced and where cell growth may occur, further providing means for removing the desired metabolic product or cells containing said product from said culture channels;
   (c) semipermeable membrane means separating said medium channels from said culture channels, said culture channels and medium channels being so dimensioned and disposed so that no cell is more than about 500 microns from the nearest source of nutrients, where each membrane contacts a plurality of culture channels and a plurality of medium channels, where each membrane has a molecular weight cutoff of at least 1000 daltons, and in which the channels have a depth of less than about 1000 microns and a width of less than about 1650 microns.

2. The cell growth system of claim 1 in which the channels are so dimensioned and disposed that no cell is more than about 200 microns from the nearest source of nutrients and the channels have a depth which does not exceed about 200 microns.

3. A method of growing cells and recovering a desired cellular product which comprises introducing cells capable of producing the product into a cell growth system according to claim 2, cultivating the cells under conditions favorable to the production of the desired cellular product, and recovering the cellular products or cells containing said products from the cell culture channels.

4. A method of growing cells and recovering a desired cellular product which comprises introducing cells capable of producing the product into a cell growth system according to claim 1, cultivating the cells under conditions favorable to the production of the desired cellular product, and recovering the cellular product or cells containing said product from the cell culture channels.

* * * * *